United States Patent [19]
Andersen et al.

[11] 4,276,263
[45] Jun. 30, 1981

[54] STERILIZATION SYSTEM

[75] Inventors: Harold W. Andersen; Shirley R. Andersen, Both of Oyster Bay; Clifford Zaner, Holbrook; Charles H. Harrison, Oyster Bay, all of N.Y.

[73] Assignee: Anprosol Incorporated, Oyster Bay, N.Y.

[21] Appl. No.: 23,493

[22] Filed: Mar. 23, 1979

Related U.S. Application Data

[62] Division of Ser. No. 924,018, Jul. 12, 1978, abandoned.

[51] Int. Cl.³ .............................................. A61L 2/18
[52] U.S. Cl. ..................................... 422/292; 134/26; 134/84; 134/88; 206/219; 206/484; 206/524.1; 206/524.2; 206/524.9; 206/525; 222/107; 222/183; 222/185; 422/7; 422/12; 422/29; 422/37; 422/119; 422/300
[58] Field of Search .................... 422/292, 300, 29, 37, 422/7, 18, 16, 119; 206/219, 484, 525, 524.1, 524.2, 524.9; 229/56; 222/107, 185, 183; 134/26, 84, 88

[56] References Cited

U.S. PATENT DOCUMENTS

| 2,248,266 | 7/1941 | Abrams | 206/484 |
| 2,460,259 | 1/1949 | Kahler | 422/17 X |
| 2,575,713 | 11/1951 | Johansson | 422/16 X |
| 2,636,501 | 4/1953 | Hilliker | 134/88 X |
| 2,767,106 | 10/1956 | Gunderson et al. | 422/16 |
| 2,872,081 | 2/1959 | Randall | 222/183 |
| 2,923,404 | 2/1960 | Adell | 206/525 |
| 3,296,145 | 1/1967 | Findlan et al. | 424/325 X |
| 3,469,768 | 9/1969 | Repko | 229/56 |
| 3,891,138 | 6/1975 | Glas | 206/484 X |

FOREIGN PATENT DOCUMENTS 781708 8/1957 United Kingdom.

OTHER PUBLICATIONS

Chemical Abstracts; vol. 84, 1976; p. 295; No. 84:48419c, p. 453; No. 84:171342b.

Primary Examiner—Barry Richman
Attorney, Agent, or Firm—Jordan and Hamburg

[57] ABSTRACT

A sterilization system preferably utilizing two baths in which articles to be sterilized are immersed into a first bath where the articles are conditioned and then into a second bath containing a sterilizing solution where they are sterilized. The ingredients for the sterilization system are stored in hermetically sealed pouches which are opened just prior to use to release and activate the system. The sterilization system utilizes a chlorine solution which is highly efficacious while being non-corrosive and having a reduced toxicity and prolonged shelf life, and may be utilized by relatively untrained personnel.

9 Claims, 5 Drawing Figures

STERILIZATION SYSTEM

This is a division of application Ser. No. 924,018, filed July 12, 1978, and now abandoned.

BACKGROUND OF THE INVENTION

Chlorine-based disinfectants have played an important role in medical history. As early as the 18th century, the bleaching and disinfecting properties of chlorine were recognized. In 1846, the efficacy was demonstrated of solutions prepared from chloride of lime for prevention of puerperal fever. Shortly thereafter, calcium hypochlorite was used for treating water. World War I promoted investigation of the use of chlorine solutions for cleansing infected wounds. In 1915, Dakin reported experiments concerning the chlorine solution which bears his name (Dakin, H.D.: The antiseptic action of hypochlorites, Brit. Med. J. ii:809 December 1915). Subsequently, the results of lavaging foul wounds with Dakin's solution were lauded.

Bacteriological studies in this century investigated vital parameters of chlorine solutions. Germicidal action depends on the concentration of hypochlorous acid (Charlton, D. & M. Levine: Germicidal properties of chlorine compounds, Iowa State College Bulletin 35:48, 1937). Both the quantity of chlorine compounds and the pH of the solution determine the concentration of hypochlorous acid. The higher the pH of a chlorinated water solution, the lower the concentration of undissociated hypochlorous acid. At pH 7.5 approximately 50% of the chlorine concentration will exist as undissociated hypochlorous acid (HOCl) while the other 50% will be present as hypochlorite ion (OCl) (White, G.C.: Handbook of Chlorination, New York, Van Nostrand Reinhold, 186, 1972). Maximum efficacy of a given concentration of chlorine in solution occurs below pH 5, when all of the chlorine present exists as undissociated hypochlorous acid. Bacteriological tests substantiate that, as hypochlorite solutions are acidified, a marked increase in germicidal action occurs. With pH control, chlorine has provided to be one of the most potent and reliable germicides. As such, it became widely used in water and sewage treatment.

Early studies elucidated a number of problems with chlorine disinfectants. Dakin (previously identified) recognized the "highly irritating character" of some chlorine solutions and learned that tissue irritation could be reduced if both the concentration of hypochlorites and the pH were controlled. Dakin discused the importance of neutralizing the solution by adding acid to the alkaline hypochlorite compound. Dakin's "neutralized" solution could be continuously applied to wounds without serious irritation.

Another problem is that chlorine solutions are very unstable. The effectiveness of these solutions deteriorates significantly within a few hours. This problem depends largely on the pH of the solution. The more alkaline a hypochlorite solution is, the less hypochlorous acid is present, the less effective it is as a sterilant, and the more stable it is. An example of such an extremely stable hypochlorite solution is ordinary household bleach. The more acid such a hypochlorite solution is, the greater is its hypochlorous acid content, the more effective it is as a sterilant, and the greater the instability of the solution. Cullen indicated that the lower limit of pH of Dakin's solution was about 9, for below that level the solution became too unstable for clinical use (Cullen, G. E. & H. D. Taylor: Relative irritant properties of the chlorine groups of antiseptics, J. Exp. Med. 28:681, 1918). Depending on the initial concentration of hypochlorite, the effective half-life of an acid solution may be only a few hours. A truly neutralized chlorine solution must be mixed immediately prior to use.

The high reactivity of chlorine creates another major problem with its use as a sterilant. Early in this century, Carrel recognized a substantial reduction in the germicidal efficacy of chlorine solutions to which blood serum had been added and remarked about the rapid disappearance of hypochlorite in contact with body tissues and fluids (Carrel, A. & G. Dehelly: The treatment of infected wounds, London, Univ. of London Press, 1918). In a more recent study, addition of only 300 ppm of lactose, a natural sugar, was found to significantly reduce the efficacy of a chlorine solution (Rudolf, A. S. & M. Levine: Factors affecting the germicidal efficacy of hypochlorite solutions, Iowa State College Bulletin, 40:35, 1941). Chlorine readily combines with a wide variety of organic and inorganic substances and is thereby inactivated. Reliable use of a chlorine-based germicide requires adequate cleansing of materials to be sterilized to remove such ubiquitous contaminants as protein or grease. That cleansing must be performed with compatible agents. Most common cleansing agents are not compatible because they bind and inactivate chlorine compounds.

Chlorine solutions have no inherent wetting or detergent capacity. Therefore, microorganisms which are encased in an air bubble or in an oil drop escape destruction. Addition of a surface active or wetting agent to the chlorine solution can increase penetration and contact. Careful evaluation is required to assure that the agent used is compatible and does not bind and inactivate significant amounts of chlorine. Addition of specific compatible detergents to chlorine solutions has been reported to increase their germicidal efficacy. (Petroff, S. A. & P. Schain: The enhancement of bactericidal properties of well known antiseptics by addition of detergents, Quart. B. Seaview Hosp. 5:378-379, 1940). Such combinations of chlorine compounds with compatible surfactants, though fine germicides, are not now generally used as sterilants because of their corrosive character.

The most difficult to solve problem of chlorine-based germicides is that they are highly corrosive. Concentrations of hypochlorous acid sufficient to sterilize standard bacteriological challenges also quickly attack metals, even stainless steel, causing discoloration and pitting. Metal instruments soaked in chlorine solutions tend to be irreversibly damaged. Sharp edges are destroyed and metal surfaces become pitted and darkened. Instrument manufacturers have been known to remark that they dislike having a product exposed to a chemical which magnifies any metallurgical flaw in even the best stainless steel. Corrosion inhibitors have been recommended for use with hypochlorites (Botham, G. H. & G. A. Dummett: Corrosion by commercial sodium hypochlorite and its inhibition, J. Dairy Res. 16:37, 1949). Sodium silicate was found to be effective in an alkaline solution containing 150 ppm available chlorine. The increase of alkalinity, however, substantially decreases germicidal efficacy. Sodium silicate insufficiently retards corrosion in more concentrated hypochlorite solutions. Many other anticorrosive agents are incompatible because they react with and inactivate chlorine. Resolution of this problem is required in order to provide a chlorine sterilant which is safe for instruments.

Dr. J. C. Kelsey investigated liquid disinfectants for many years. He developed the "Kelsey-Sykes" test, which is now the British referee bacteriological challenge test. In recent years, Dr. Kelsey recommended sodium hypochlorite solutions as the most efficacious liquid disinfectants. He tried to develop an optimal chlorine solution and published a report of his work in 1974 (J. Clin. Path. 27, 632–638). The chlorine solution which he recommends in that article is highly toxic because of its methanol content and its unadjusted alkaline pH. It is also extremely corrosive.

Since Dr. Kelsey retired, Dr. David Coates has carried on the work on hypochlorite solutions. He published a report of his work in 1978 (J. Clin. Path. 31, 148–152). Further experiments indicated that the hypochlorite solutions which he had reported in that publication, were too corrosive for routine use. Therefore, to control the corrosive and tissue-irritating properties of the solution, Dr. Coates reduced the concentrations of alcohol and of available chlorine (to about 200 ppm). He has also learned that buffering the pH of the solution is vital. The chlorine solution which he has most recently recommended, however, contains neither a satisfactory surfactant nor an anti-corrosive agent.

Despite the long history of efficacious use of chlorine compounds as disinfectants, few chlorine compounds today are used as sterilants in medical practice. None of the existing solutions meet the requirements of an optimal chlorine-based sterilizing system. The ideal characteristics of such a system are the following:

1. It must reliably kill the standard U.S. Government bacteriological challenge (called the "AOAC" test), preferably within a contact time of 30 minutes or less. Existing liquid sterilants require contact times of many hours to pass the "AOAC" test.

2. It must be completely non-corrosive and non-damaging within the recommended contact time.

3. Its pH must be adjusted to and maintained at approximately neutral in order to increase efficacy, reduce toxicity, and avoid the rapid deterioration of potency which occurs in more highly acid chlorine solutions.

4. It must assure proper preparation of materials to be sterilized, in a way which avoids contamination by organic material or chemicals which might inactivate the chlorine.

5. The system must be so simple that even untrained personnel can prepare and use it without significant error.

In order to maintain the pH of a solution within a desired range, buffers are usually used. One of the most common buffers in the neutral range contains phosphates. For buffering purposes, less than 1% of phosphates will suffice. A solution containing 0.2% hypochlorite, buffered at pH 7.5 with phosphates, is an efficacious sterilant. Such a solution, however, is corrosive and has undesirable surface tension characteristics.

Many investigators have used standard concentrations of phosphates to buffer chlorine solutions (e.g. Friberg, L. & E. Hammarstrom: The action of available chlorine on bacteria and bacterial viruses, Acta. Pathl. Microbiol. Scand., 38:128, 1956). Phosphates are included in lists of corrosion inhibitors (Uhlig, H.H: The Corrosion Handbook, NY, Wiley & Sons, 906-7 and 913-14, 1948). Concentrations of phosphates under 1% have been added to chlorine-based disinfectants to reduce corrosion (Diversol BX, Brit. Pat. No. 781 708). However, it has not heretofore been known to use concentrations of phosphates over 1% to achieve substantial corrosion control.

According to the present invention, it has been determined that concentrations to phosphates in excess of 1% markedly reduce the corrosiveness of the solution. The concentration of phosphates necessary to control corrosion depends on several factors including the concentration of hypochlorite, the pH, the presence of a surface active agent, the contact time, and the type of steel. In a solution at pH 7.5 containing 0.02% sodium hypochlorite and a compatible surface active agent, addition of a total of 1.17% phosphates produces a 93% reduction in the corrosion of carbon steel during 4 hours contact. In a similar solution containing 0.2% sodium hypochlorite, addition of a total of 2.75% phosphates produced a 97% reduction in the corrosion of carbon steel during 2 hours contact. When the concentration of total phosphates in the latter solution was increased to approximately 7%, no notable corrosion of common steel occurred. In this instance, even 24 hours of soaking of common steel produced no visible change.

The combination of phosphates in the solution acts as a buffer, resisting alteration in the pH. The concentrations of acid and alkaline phosphates are adjusted to produce approximate neutrality. Under this circumstance, a solution containing as high a hypochlorite concentration as 0.2% exhibits little tendency to tissue irritation. When that solution is repeatedly dropped into the eyes of rabbits, according to directions for the Draize test, no evidence of inflammation occurs (see Example IX).

According to the present invention a surface active agent is included in the chlorine solution. Air bubbles on material not only prevent sterilization but also promote corrosion. The addition of a detergent reduces surface tension and helps avoid formation of bubbles. Few detergents, however, are compatible with both chlorine and phosphates and also effective at pH 7.5. Some effective surfactants which do not react with chlorine, for example, combine with the phosphates causing precipitation. A nonionic agent which meets the desired requirements is a 12 carbon alkyldimethyl amine oxide, for example, dimethyl lauryl amine oxide (see U.S. Pat. No. 3,296,145). This amine oxide is available under the following trademarks: Ammonyx LO and Barlox 12.

The addition of this amine oxide to the sterilizing system of the present invention increases the efficacy of the solution. Suture loops placed on the surface of a buffered chlorine solution lacking detergent will float. If the loops are forced under the surface, many tiny bubbles are visible on their surfaces. When a solution contains an adequate surfactant, the loops rapidly sink into the solution without visible bubbles. With the addition of the amine oxide, solutions of the present invlention exhibit adequate surface tension characteristics (see Example VIII).

Inclusion of the surfactant in the sterilizing system of the present invention also measurably enhances corrosion inhibition. For example, when approximately 5% phosphates are added to a solution containing 0.2% hypochlorite at pH 7.5, an 85% reduction in corrosion occurs. When dimethyl lauryl amine oxide is then added to that combination, corrosion virtually ceases. Some surface active agents are listed among corrosion inhibitors (Uhlig, H.H.: The Corrosion Handbook, New York, Wiley & Sons, 910–911). However, no previous report is known of potentiation of corrosion inhibition by a combination of phosphates and a surface active agent added to a chlorine-based sterilizing system.

In order to avoid inactivation of the germicidal solution by contaminants such as inorganic salts, organic material or incompatible detergents, and assure thorough wetting of the instrument to be sterilized, imersion in a conditioning bath may be added to the sterilizing system. The conditioning bath consists of ample quantities of separate washing composition containing the same amine oxide as well as agents to control corrosion and pH. Thus, all materials to be sterilized would be preconditioned in a solution containing the conditioning composition. Transfer of small amounts of the conditioning solution to the sterilizing solution will not counteract the efficacy of the latter.

Shelf-life requirements necessitate that the major components of the sterilizing solution (hypochlorite, phosphates and surfactant) remain separate until mixed for use. To avoid errors in preparation, a compartmented bag was devised which assures complete mixing of all components when the bag is opened. A colored indicator added to the component in the center compartment acts as a safeguard. Alteration in the central color of the package warns the user that leakage between compartments has occurred. The indicator color immediately disappears when combined with small quantities of hypochlorite. To complete the sterilizing solution, the three compartments in the package are added to a measured amount of water.

Bacteriological tests on a specific formulation of the sterilization system, Solution Q (see Examples V-VII) prove it to be a remarkable germicide. High titres of vegetative organisms are killed within minutes. The solution readily passed Great Britain's referee challenge, the "Kelsey-ykes" test (Kelsey, J. C. & I. M. Maurer: An improved (1974) Kelsey-Sykes test for disinfectants. Pharm. J., Nov. 30, 1974). The sterilization system of the present invention can reliably pass within 30 minutes the American "AOAC Sporicidal Test" which often represents the most difficult bacteriological hurdle. Although some decay in available chlorine occurs during the 24 hours useful life of the solution, that change is insufficient to affect germicidal potency. A 24-hour old solution also passes the "AOAC Sporicidal Test".

Accordingly, an object of the present invention is to provide a sterilization sytem which is efficacious as a sterilant, which is non-corrosive and non-damaging, which has no deleterious effects on instruments within the recommended contact time, has little tissue irritating properties, has good wetting capacity, and which is stable for more than twenty-four hours.

Another object is to provide a reliable liquid sterilant system operable within a short enough cycle for practical application.

Another object is to provide a liquid sterilant of increased efficacy, reduced toxicity and prolonged life in which the potency does not rapidly deteriorate.

Another object is to provide a sterilization system which does not become contaminated by the materials being sterilized.

A further object is to provide a sterilization system which is so simple that even untrained personnel can prepare and use it without significant chance of error.

DESCRIPTION OF THE PREFERRED EMBODIMENTS

Figure 1:
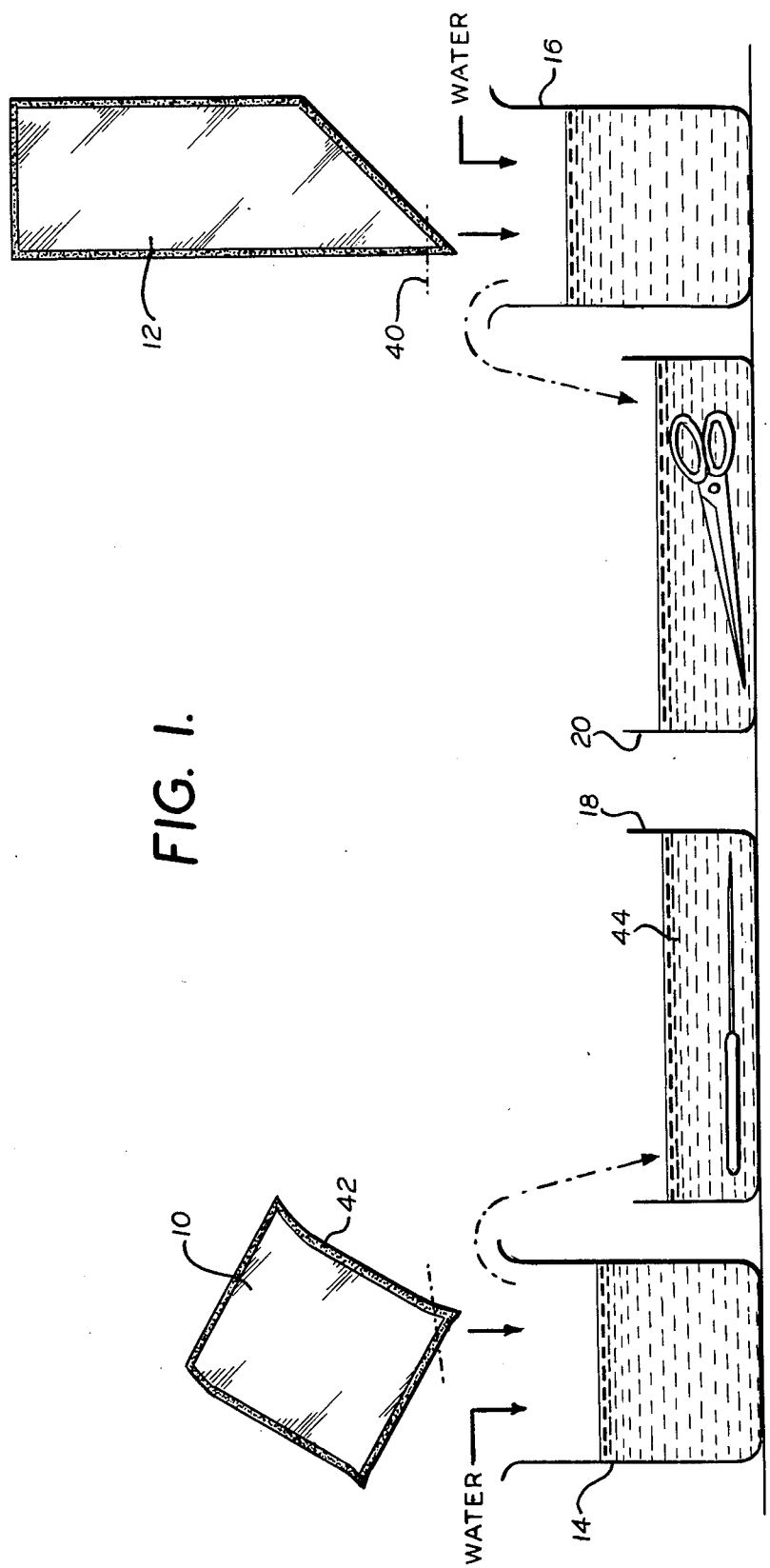
FIG. 1 is a schematic view illustrating one embodiment of the sterilization system of the present invention.

Referring to the drawings, FIG. 1 shows an overall view of one embodiment of the sterilizing system of the present invlention. The illustrated sterilization system involves the use of two sealed plastic pouches 10 and 12. The entire contents of each pouch 10, 12 are mixed with water in the containers 14, 16 respectively and the contents of the containers 14, 16 are then emptied into wide mouth containers or pans 18, 20 respectively which define two baths in which the sterilization process is performed as will be described.

Figure 2:
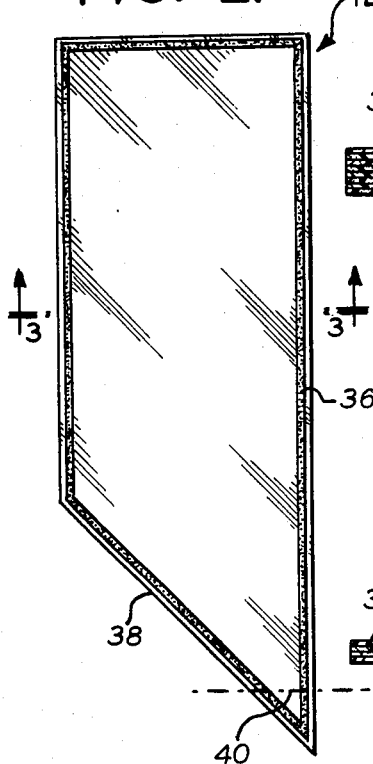
FIG. 2 is an elevational view of the tri-pouch used in the sterilization system of the present invention.

In the illustrated embodiment, FIG. 2, the contents of the first pouch (10) used for the first bath contains cleaning and conditioning agents. The second pouch (12) for the second bath is a tri-pouch in that it consists of three separate, sealed compartments 22, 24, 26 in which one outer compartment (22 or 26) contains a hypochlorite solution, the other outer compartment (22 or 26) contains a buffer and anticorrosive agent, and the intermediate compartment (24) sandwiched there between contains a surfactant or wetting agent preferably with a color indicator.

Turning to details of the illustrated embodiment, the tri-pouch (12) may be made from four sheets of plastic film (31, 32, 33, 34,) which may be superimposed one on top of the other and heat sealed together at their edges (36) to form a pouch having the three separate compartments (22, 24, 26). Each of the three separate compartments (22, 24, 26) is completely sealed from one another such that the three liquid components will be kept separate until the moment of use of the sterilization system.

Figure 3:
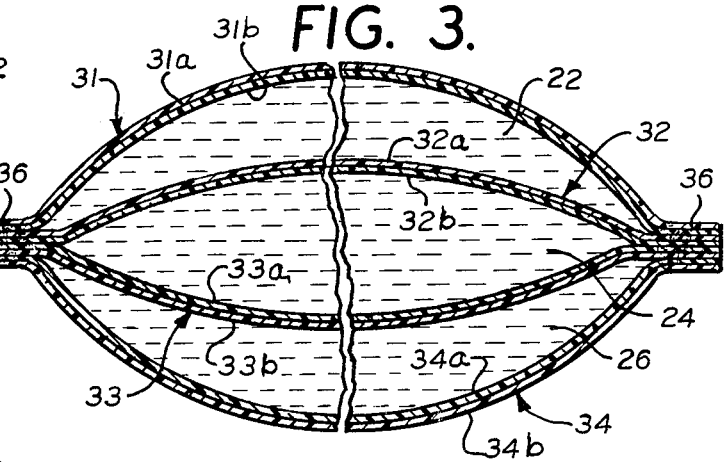
FIG. 3 is a sectional view taken along the lines 3—3 in FIG. 2.
Figure 4:
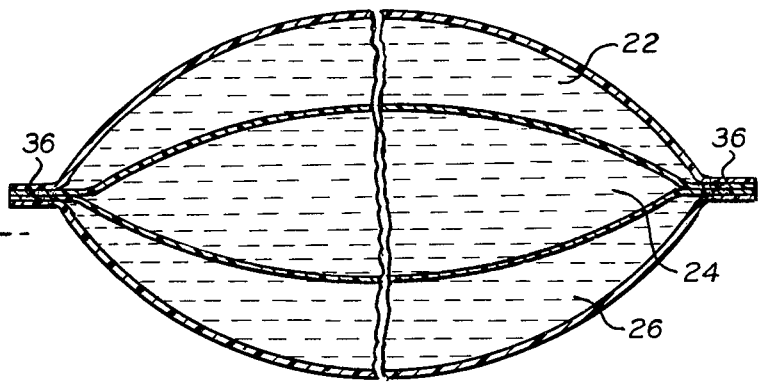
FIG. 4 is a sectional view similar to FIG. 3 of an alternate arrangement.

The sheets of plastic film (31-34) of the tri-pouch (12) may each be made of a double thickness film as illustrated at 31a, 31b, 34a, 34b respectively in FIG. 3 to provide added integrity to prevent leakage through any pin holes which may occur during manufacture of single thickness plastic film. The term double thickness may refer to what is commercially known as coextruded or laminated film.

The tri-pouch (12) has a portion with converging side seams to form a tapered or funnel-like end portion (38) as shown in the drawings. To release the three liquid components from the tri-pouch (12), it is only necessary to snip off the pointed end of the tri-pouch (as indicated at 40) with a pair of scissors or the like to simultaneously cut through all three compartments. Accordingly, the liquid contents of all three compartments (22, 24, 26) of the tri-pouch will pour out simultaneously, thereby mixing the three components and activating the sterilization system. The contents of the tri-pouch (12) are emptied into the previously mentioned container (16) which contains water or to which water is added. Thereafter the contents of the container (16) is emptied into the pan (20) forming the second bath. The use of the tri-pouch (12) permits storage of the correct and premeasured amounts of the separated liquids until ready for use.

As previously indicated, when it is desired to use the sterilization system, the tapered end (34) of the tri-pouch (12) is merely snipped off and the three liquid ingredients will pour out simultaneously to mix during the pouring operation. Thus, the use of the three compartment pouch greatly reduces the chance of a partial mixing and virtually prevents use of less than all of all three of the components of the tri-pouch.

The arrangement of the tri-pouch also has the advantage that if either the liquid sterilant or the buffer should leak internally, they would leak into center compartment (24) containing the wetting agent and the color indicator to effect a color change and thereby provide a visual indication that a leak has occurred. By way of example, the color indicator may be chlorophenol red solution which gives the center compartment (24) a reddish purple color. If the liquid sterilant solution (e.g. hypochlorite) in one of the outer compartments, 22 or 26, were to leak into the center compartment (24), the chlorine/hypochlorite would oxidize the reddish purple color indicator and the package would appear as a pale straw yellow of the hypochlorite solution. Conversely, should the buffer and anticorrosive solution (e.g. phosphate) in the other of the outer compartments, 22 or 26, leak internally, it would cause a precipitate to occur in the center compartment (24). Thus, the absence of the reddish purple color or the presence of the precipitate would be an indication that an internal leak has occurred. The color indicator is thereby able to provide a visual determination of whether or not an internal leak has occurred at any time between the filling of the tri-pouch (12) to the time it is ready for use. Accordingly, assurance is readily provided to the user that no internal leakage has occurred and that the contents of the tri-pouch are safe to use.

The walls (31–34) of the tri-pouch (12) are made of a clear plastic film so that the contents can be readily observed. By way of example, the plastic film may be polyethylene, polyethylene-ionomer coextrusion, polyethylenepolyamide laminate, or the like and may have a thickness of from 0.002 in. to 0.020 in., preferably 0.006 in.

Figure 5:
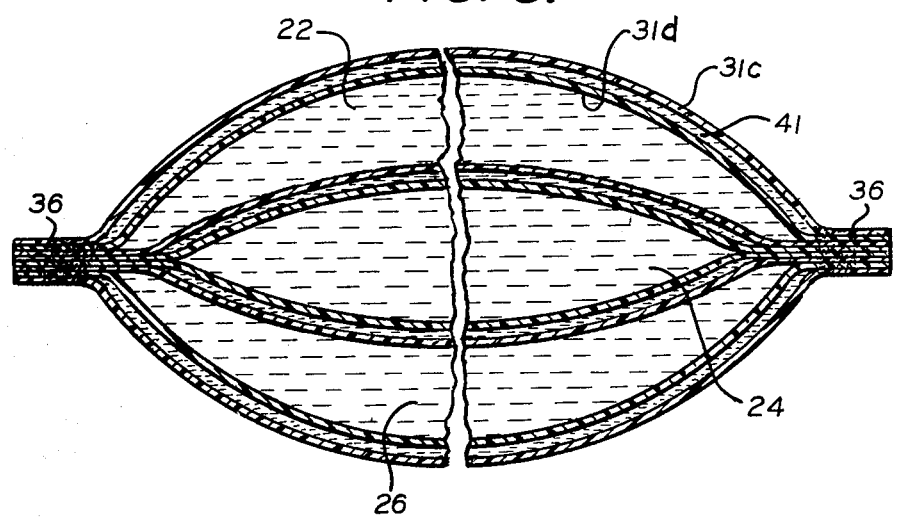
FIG. 5 is a sectional view similar to FIG. 3 of a further alternate arrangement.

As an alternate arrangement, the membranes or septa of the tri-pouch could be of a double thickness such as indicated, for example, at 31c and 31d in FIG. 5, with various color indicators interposed between the two thicknesses as indicated at 41, to provide further and easily detected indication of a leak in one of the inner septa.

The pouch (10) containing the cleansing and conditioning agents may also be made of a clear plastic film and heat sealed around the edges (44). By way of example, the plastic film may be polyethylene, polyethylene-ionomer coextrusion, polyethylene-polyamide laminate, or the like and may have a thickness of from 0.002 in. to 0.020 in., preferably 0.006 in.

Returning to FIG. 1, when it is desired to sterilize, the first pouch (10), containing the cleansing and conditioning agent, is opened and emptied into the container (14). Tap water is then added to the container (14) to bring the mixed contents to a given quantity of solution as may be indicated by marks on the container (14). The resulting diluent is then poured into the pan (18) to provide a bath in which the various items to be sterilized may be conditioned prior to immersion in the sterilizing solution.

Similarly, the tri-pouch (12) is snipped off at 40 by a pair of scissors as previously described and all three liquid components simultaneously emptied into the container 16. As with the first pouch (10), the container (16) is then filled with clear tap water to a mark which may be provided on the container (16) and the resulting diluent subsequently poured into the second bath (20).

The items to be sterilized (44) are first immersed into the first pan (18) wherein such items are conditioned and then immersed into the second pan (20) where they are sterilized.

The purpose of the first bath containing the cleansing and conditioning agents is to clean the instruments to be sterilized by removing such ubiquitous organic contaminants as proteins or grease, to dilute and neutralize inorganic contaminants which otherwise might react with the sterilant, and to thoroughly wet the surfaces of the item to be sterilized. This conditioning solution is utilized because the chlorine in the second bath readily combines with a wide variety of organic and inorganic substances and is thereby inactivated. Thus, the conditioning in the first bath (10) is performed with a cleaning agent which is compatible with chlorine, a 12 carbon alkyldimethyl amine oxide, for example, dimethyl lauryl amine oxide, which may be obtained, for example, from Onyx Chemical Company, Division of Millmaster Onyx. Corp. of Jersey City, N.J., under the name of "Ammonyx LO", and which is set forth in U.S. Pat. No. 3,296,145. Also contained in the first bath are potassium pyrophosphate and tripotassium phosphate which serve to saponify oily substances, sequester metallic ions, deflocculate particles, act as anticorrosive agents, and aid in the pH control of the solution. Pylam turquoise blue acts as a coloring agent and may be omitted or another coloring agent may be substituted.

An example of a specific composition in the first pouch (10) is:
7.5 g. potassium pyrophosphate
7.5 g. tripotassium phosphate
38 ml. dimethyl lauryl amine oxide (30% active)
0.0128 g. Pylam turquoise blue
60 ml. tap water The first bath is readily prepared by mixing the contents of first pouch (10) with 3.3 liters of tap water to form 3.4 liters of solution. If the amounts are doubled, 6.8 liters of solution are obtained, etc.

The second aqueous bath in the pan (20) desirably comprises:
0.02 to 1% of an alkali metal or alkaline/earth metal hypochlorite
0.1 to 0.5% of a nonionic surfactant which is compatible with chlorine and phosphates (30% active)
1.4 to 20% of di (alkali metal) phosphate
titrated to a pH of 7.0 to 8.0 with mono (alkali metal) phosphate, with the proviso that the lower limit of di (alkali metal) phosphate is 4.0% when the amount of said hypochlorite is from 0.5 to 1%, these percentages being based on the weight of the ingredient (in grams) per 100 ml of solution. The amount of mono (alkali metal) phosphate required to obtain the indicated pH ranges from 0.08 to 21%. The use of 0.05 to 0.3% of sodium hypochlorite, 0.2 to 0.4% of dimethyl lauryl amine oxide (30% active), 2 to 13% of dipotassium phosphate, titrated with monopotassium phosphate to a pH from 7.2 to 7.7 are preferred. The amount of monopotassium phosphate required to obtain the indicated pH ranges from 0.33 to 9.66%.

As an example, to obtain the aforementioned second bath, one of the outer compartments, say outer compartment 22, of the tri-pouch suitably contains 136 ml of 6% sodium hypochlorite.

The other outer compartment (26) suitably has the following contents:
314 ml. water
360 g. dipotassium phosphate
80 g. monopotassium phosphate
0.12 g. sodium chromate The chromate is used as a colorant and can be replaced by other colorants which do not react adversely with the chlorine. The chromate can alternatively be added to the hypochlorite compartment or can be omitted.

The center compartment (24) of the tri-pouch (12) suitably has the following contents:
14.1 ml. dimethyl lauryl amine oxide (30% active)
5.2 ml. 0.04% chlorophenol red solution
80.7 ml. water If the color of the chlorophenol red disappears, this means that the solution from at least one of the outer compartments has leaked into the center compartment (24). In this case, the affected tri-pouch should be discarded. Colorants other than chlorophenol red can be used so long as they do not adversely affect the final chlorine bath.

The second bath is readily prepared by mixing the contents of the sealed compartments of the tri-pouch (12) with 3.3 liters of water to form 4 liters of solution. If the amounts are doubled, 8 liters of solution are obtained, etc.

The recommended concentration of 0.2% hypochlorite provides an extremely generous safety margin. The solution is still fully effective when it is 24 hours old though it contains about one-third less available chlorine. Generally, the solution will be effective for 48 to 72 hours.

The pH of the second bath preferably is 7.5 to provide minimum tissue irritancy, although it may vary from 7.0 to 8.0. In addition to controlling pH, the phosphates act as saponifiers and cleaning agents.

In operating the invention, the instruments to be sterilized may be immersed into the first bath (18) for a period on the order of 2 minutes and then are transferred to the second bath where sterilization is affected in 15–30 minutes. As previously indicated, transfer of small amounts of the cleansing solution from the first bath to the second bath will not counteract the efficacy of the sterilant.

As an indication of the uniqueness of a 12 carbon alkydimethyl amine oxide as a surfactant in the sterilizing compositions of this invention, the following surfactants were found to be incompatible with sodium hypochlorite or hypochlorous acid:

| TRADEMARK | IONIC TYPE | DESCRIPTION |
|---|---|---|
| Aerosol OS | anionic | sodium isopropyl napthalene sulfonate |
| Advawet #33 | nonionic | fatty acid ester glycol |
| Advawet #43 | nonionic | fatty acid ester glycol |
| Ammonyx CDO | *nonionic | coco amido propyl dimethyl amine oxide |
| Avirol 300 | anionic | triethanolamine alkyl sulfate |
| Avirol 116-E | anionic | sodium lauryl ether sulfate |
| Chemadene 300 | amphoteric | amine salt |
| Cerfak 1400 | anionic | alkyl polyoxyethylene ether |
| Cordon 300 | anionic | sulfated oil |
| Detersol T-Special | | pine oil detergent |
| Emkapon TS | anionic | amide sulfonate |
| Emkatex AA | anionic | alkyl aryl sulfonate |
| Foamole AR | nonionic | coconut oil alkanol amide |
| Gafac RA-600 | anionic | free acid of complex organic phosphate ester |
| Klearfac AA-250 | anionic | free acid of organic phosphate ester |
| Lonzaine 12-C | amphoteric | coco alkyl amino betaine |
| Miranol JEM | amphoteric | dicarboxylic octoic sulfonated amine |
| Miranol JS | amphoteric | carboxylated sulfonated amine of octoic acid |
| Maprofix 60-S | anionic | sodium lauryl ether sulfate |
| Merpol HC | nonionic | ETO condensate of long chain of fatty alcohol |
| Monoflor 52 | nonionic | fluorohydrocarbon |
| Nopcowet 50 | anionic | sulfonated alkyl ester |
| Olapon ND-100 | nonionic | polyethylene glycol ether of linear alcohol |
| Pleurafax A-38 | nonionic | straight chain aliphatic oxy-alkylated alcohol |
| Pleuronic L-64 | nonionic | ethylene oxide condensate |
| Richonate TAB | anionic | triethanolamine dodecyl benzene sulfonate |
| Richonate 45-B | anionic | sodium dodecyl benzene sulfonate |
| Rueterg 97-S | anionic | alkyl aryl sulfonate |
| Sellogen concentrate | anionic | methyl taurine condensate |
| Siponic L-4 | nonionic | ethoxylated lauryl alcohol |
| Standapol AB-45 | amphoteric | alkyldimethyl betaine |
| Standapol ES-3 | anionic | sodium lauryl ether (3 moles ETO) sulfate |
| Standapol OLB-50 | amphoteric | betaine |
| Standamox 01 | nonionic | oleyl dimethyl amine oxide |
| Tamol SN | anionic | sodium napthalene sulfonate |
| Triton X-114 | nonionic | octyl phenoxypolyethoxyethanol |
| Tween 20 | nonionic | polyoxyethylene (20) sorbitan monolaurate |

-continued

| TRADEMARK | IONIC TYPE | DESCRIPTION |
|---|---|---|
| Tween 80 | nonionic | polyoxyethylene (20) sorbitan mono-laurate sodium amine phosphate |
| Wayhib S | anionic | sodium amine phosphate |
| Zonyl FSN | nonionic | fluorocarbon complex |
| Zonyl FSA | anionic | fluorohydrocarbon complex |
| | | All cationic surfactants |

*nonionic above pH 7, cationic below pH 7

The following surfactants were found to be compatible with hypochlorite solutions but incompatible with the concentration of phosphate in test Solution Q (see Example V):

| TRADEMARK | IONIC TYPE | DESCRIPTION |
|---|---|---|
| Abex 18-S | anionic | |
| Ammonyx MO | nonionic* | |
| Ammonyx MCO | nonionic* | |
| Tetranol | anionic | sulfated fatty ester |
| Gemtex HC-70 | anionic | sodium dihexyl sulfosuccinate |
| Standapol ES-2 | anionic | sodium lauryl ether (2 moles ETO) sulfate |
| Sipon LSB | anionic | sodium lauryl sulfate |
| Mersonol 840 | anionic | sodium dihexyl sulfosuccinate |
| Aerosol OT-100 | anionic | sodium dioctyl sulfosuccinate |
| Standapol WAQ | anionic | sodium lauryl sulfate |
| Triton X-301 | anionic | sodium alkyl aryl polyether sulfate |
| Carbanone BD | anionic | carboxylated polyethoxy of linear alcohol |
| Monoflor-31 | anionic | fluorohydrocarbon complex |
| Aerosol CT | | |
| Triton X-200 | anionic | sodium alkyl aryl polyether sulfonate |
| Siponic E-2 | nonionic | ethoxylated (2 moles ETO) cetyl stearyl alcohol |
| Steol CS-46 | anionic | sodium coconut ether sulfate |
| Petrowet R | anionic | sodium hydrocarbon sulfonate |
| Alkanol 189-S | anionic | sodium hydrocarbon sulfonate |
| Victawet 35-B | anionic | polyphosphate of aliphatic group |
| Victawet 58-B | anionic | phosphorated higher alcohol** |

*nonionic above pH 7
**cloudy when sodium hypochlorite is added

The uniqueness of phosphates as corrosion inhibitors for use in hypochlorite solutions is indicated by the following investigative results. The following corrosion inhibitors do not completely inhibit the corrosion caused by hypochlorite solutions.

1. Sodium silicate is an alkaline salt. It raises the pH of the chlorine solutions to 10.5. Lowering the pH causes the formation of insoluble silicic acid, which is a very weak acid having a dissociation constant of $2 \times 10^{-10}$. Sodium silicate inhibits corrosion in its alkaline environment (Botham, G. H. & G. A. Dummet, Corrosion by commercial sodium hypochlorites and its inhibition, J. Dairy Res., 16:23, 1949) but the undissociated silicic acid has no corrosion inhibiting properties because of its low solubility.

2. Sodium molybdate was found to reduce corrosion of sodium hypochlorite solutions at a pH of 7.5 to 8, but it did not completely eliminate corrosion when tested up to a concentration of 10%. Sodium molybdate does not bind free chlorine.

3. Zinc ions form insoluble zinc hydroxide at pH 7.5 and, therefore, are of no use as a corrosion inhibitor for use in hypochlorite solutions. The dissociation constant for zinc hydroxide is $9.6 \times 10^{-4}$ and it is insoluble in water.

4. Sodium chromate was found to reduce corrosion of sodium hypochlorite solutions at a pH of 7.5 to 8, but did not completely eliminate corrosion when tested up to a concentration of 1%. Sodium chromate is toxic in high concentrations.

5. Sodium sulfite is a reducing agent and will reduce $Cl+$ to $Cl-$.

6. Sodium nitrite is a reducing agent and will reduce $Cl+$ to $Cl-$.

7. The surfactant, Chemadene 300, was found to eliminate corrosion when used in high concentrations, but it was also found to bind free chlorine.

The following are exemplifications of various aspects of this invention.

EXAMPLE I

Controlling Corrosion of Metals in Sodium Hypochlorite Solutions

PURPOSE

The purpose of this experiment is to demonstrate the corrosion inhibiting effect of increasing concentrations of mono and dipotassium phosphate in sodium hypochlorite solutions, with and without a nonionic surface active agent.

MATERIALS
1. Sodium hypochlorite (Purex Bleach)
2. Monopotassium phosphate (KH2PO4)
3. Dipotassium phosphate (K2HPO4)
4. Dimethyl lauryl amine oxide (30% active)
5. Disposable carbon steel scalpel blades, #11 (Fisher Scientific Cat. #9-916-B)

TEST SOLUTIONS
A. 0.2% NaOCl—(pH 10.5)
B. 0.2% NaOCl, 0.35% amine oxide—(pH 10.5)
C. 0.2% NaOCl, 0.24% KH2PO4—(pH 7.5)
D. 0.2% NaOCl, 0.24% KH2PO4, 0.35% amine oxide—(pH 7.5)
E. 0.2% NaOCl, 0.43% KH2PO4, 0.5% K2HPO4—(pH 8.5)
F. 0.2% NaOCl, 0.43% KH2PO4, 0.5% K2HPO4, 0.35% amine oxide—(pH 7.5)
G. 0.2% NaOCl, 0.55% KH2PO4, 1% K2HPO4—(pH 7.5)
H. 0.2% NaOCl, 0.55% KH2PO4, 1% K2HPO4, 0.35% amine oxide—(pH 7.5)
I. 0.2% NaOCl, 0.75% KH2PO4, 2% K2HPO4—(pH 7.5)
J. 0.2% NaOCl, 0.75% KH2PO4, 2% K2HPO4, 0.35% amine oxide—(pH 7.5)
K. 0.2% NaOCl, 1.02% KH2PO4, 4% K2HPO4—(pH 7.5)
L. 0.2% NaOCl, 1.02% KH2PO4, 4% K2HPO4, 0.35% amine oxide—(pH 7.5)
M. 0.2% NaOCl, 1.18% KH2PO4, 6% K2HPO4—(pH 7.5)
N. 0.2% NaOCl, 1.28% KH2PO4, 6% K2HPO4, 0.35% amine oxide—(pH 7.5)
O. 0.2% NaOCl, 1.35% KH2PO4, 8% K2HPO4—(pH 7.5)

P. 0.2% NaOCl, 1.35% KH2PO4, 8% K2HPO4, 0.35% amine oxide—(pH 7.5)

PROCEDURE

Sixteen pairs of #11 surgical disposable carbon steel scalpel blades were accurately weighed on a micro balance. Each pair of blades was put into a separate test solution and the blades were allowed to soak for two hours. At the end of the soaking period, any corrosion products formed on the blades were washed off. The blades were then room air dried for one hour and each pair was reweighed on the micro balance. The weight loss for each pair of blades was computed.

RESULTS

TABLE NO. 1

| TEST SOLUTIONS | INITIAL WEIGHT | FINAL WEIGHT | WEIGHT LOSS | % WEIGHT LOSS |
|---|---|---|---|---|
| A | 732.32 mg. | 728.50 mg. | 3.82 mg. | 0.522% |
| B | 740.49 mg. | 737.31 mg. | 3.18 mg. | 0.429% |
| C | 755.21 mg. | 752.24 mg. | 2.97 mg. | 0.393% |
| D | 758.10 mg. | 756.12 mg. | 1.98 mg. | 0.261% |
| E | 753.37 mg. | 751.74 mg. | 1.63 mg. | 0.216% |
| F | 750.60 mg. | 749.30 mg. | 1.30 mg. | 0.173% |
| G | 735.15 mg. | 731.70 mg. | 3.45 mg. | 0.469% |
| H | 740.09 mg. | 738.12 mg. | 1.97 mg. | 0.266% |
| I | 727.00 mg. | 726.42 mg. | 0.58 mg. | 0.080% |
| J | 753.91 mg. | 753.81 mg. | 0.10 mg. | 0.013% |
| K | 742.96 mg. | 742.18 mg. | 0.78 mg. | 0.105% |
| L | 750.93 mg. | 750.92 mg. | 0.01 mg. | 0.001% |
| M | 753.15 mg. | 753.14 mg. | 0.01 mg. | 0.001% |
| N | 752.18 mg. | 752.18 mg. | 0.00 mg. | 0.000% |
| O | 755.31 mg. | 755.30 mg. | 0.01 mg. | 0.001% |
| P | 735.65 mg. | 735.65 mg. | 0.00 mg. | 0.000% |

TABLE NO. 2

| TEST SOLUTION | SCALPEL WEIGHT LOSS | % CORROSION INHIBITION FROM "A" |
|---|---|---|
| A | 3.82 mg. | — |
| B | 3.18 mg. | 16.8% |
| C | 2.97 mg. | 22.3% |
| D | 1.98 mg. | 48.2% |
| E | 1.63 mg. | 57.3% |
| F | 1.30 mg. | 66.0% |
| G | 3.45 mg. | 9.7% |
| H | 1.97 mg. | 48.4% |
| I | 0.58 mg. | 84.8% |
| J | 0.10 mg. | 97.4% |
| K | 0.78 mg. | 79.6% |
| L | 0.01 mg. | 99.7% |
| M | 0.01 mg. | 99.7% |
| N | 0.00 mg. | 100.0% |
| O | 0.01 mg. | 99.7% |
| P | 0.00 mg. | 100.0% |

CONCLUSION

A solution of 0.2% sodium hypochlorite in water was very corrosive to the steel scalpel blades. The addition of the amine oxide to the hypochlorite reduced the corrosion by 16.8%.

Buffering the sodium hypochlorite solution to pH 7.5 with monopotassium phosphate reduced the corrosion by 22.3%. The addition of amine oxide further reduced the corrosion of the buffered hypochlorite by 33.3%. The amine oxide, therefore, reduced the corrosion twice as much in the buffered hypochlorite than it did in the unbuffered hypochlorite.

The addition of increasing amounts of dipotassium phosphate to the sodium hypochlorite solution, and buffering the solution to a pH of 7.5 with monopotassium phosphate, showed increasing corrosion inhibition (see Table No. 2). The addition of amine oxide showed greatly increasing inhibition with increasing concentrations of phosphate. Only the combination of phosphates and amine oxide completely eliminated the corrosion of the steel disposable scalpel blades caused by the sodium hypochlorite.

EXAMPLE II

Controlling Corrosion of Metals in NaOCl Solution

PURPOSE

The purpose is to establish the inhibiting effect of increasing concentrations of mono and dipotassium phosphate in sodium hypochlorite solutions, with and without a surface active agent.

MATERIALS

1. Sodium hypochlorite (Purex Bleach)
2. Monopotassium phosphate (KH2PO4)
3. Dipotassium phosphate (K2HPO4)
4. Dimethyl lauryl amine oxide (30% active)
5. Disposable scalpel blades, #21 (Fisher Scientific Co. Cat. #8-918-B)

TEST SOLUTIONS

A' 0.02% NaOCl (pH 10.05)
B' 0.02% NaOCl, 0.35% amine oxide (pH 9.8)
C' 0.02% NaOCl, 0.033% KH2PO4 (pH 7.5)
D' 0.02% NaOCl, 0.033% KH2PO4, 0.35% amine oxide (pH 7.5)
E' 0.02% NaOCl, 0.25% K2HPO4, 0.058% KH2PO4 (pH 7.5)
F' 0.02% NaOCl, 0.25% K2HPO4, 0.058% KH2PO4, 0.35% amine oxide (pH 7.5)
G' 0.02% NaOCl, 0.5% K2HPO4, 0.117% KH2PO4 (pH 7.5)
H' 0.02% NaOCl, 0.5% K2HPO4, 0.117% KH2PO4, 0.35% amine oxide (pH 7.5)
I' 0.02% NaOCl, 1.0% K2HPO4, 0.192% KH2PO4 (pH 7.5)
J' 0.02% NaOCl, 1.0% K2HPO4, 0.192% KH2PO4, 0.35% amine oxide (pH 7.5)
K' 0.02% NaOCl, 2.0% K2HPO4, 0.433% KH2PO4 (pH 7.5)
L' 0.02% NaOCl, 2.0% K2HPO4, 0.433% KH2PO4, 0.35% amine oxide (pH 7.5)

PROCEDURE

Twelve pairs of #21 surgical disposable scalpel blades were accurately weighed on a micro balance. Each pair of blades was put into a separate test solution and the blades were allowed to soak for two hours. At the end of the soaking period, any corrosion products formed on the blades were washed off. The blades were then room air dried for at least one hour and each pair was reweighed on the micro balance. The weight loss for each pair of blades was computed.

RESULTS

TABLE 3

| Test Solution | Initial Weight | Final Weight | Weight Loss | Visible Observations |
|---|---|---|---|---|
| A' | 2061.79 mg | 2059.29 mg | 2.50 mg | general rusting |
| B' | 2014.84 mg | 2014.20 mg | 0.64 mg | many small pits with rust |
| C' | 2017.10 mg | 2013.65 mg | 3.45 mg | general rusting more than A' |
| D' | 2004.59 mg | 2002.98 mg | 1.61 mg | pitting and streak rusting |
| E' | 1975.16 mg | 1973.37 mg | 1.79 mg | colorful streak-like corrosion |
| F' | 1998.42 mg | 1997.35 mg | 1.07 mg | medium large pits, tarnishing |
| G' | 1970.39 mg | 1969.37 mg | 1.02 mg | medium large pits, tarnishing |

TABLE 3-continued

| Test Solution | Initial Weight | Final Weight | Weight Loss | Visible Observations |
|---|---|---|---|---|
| H' | 1990.17 mg | 1989.40 mg | 0.77 mg | medium pits, tarnished |
| I' | 1998.35 mg | 1997.64 mg | 0.71 mg | small pits, some tarnishing |
| J' | 2018.52 mg | 2018.02 mg | 0.50 mg | few small pits |
| K' | 2006.45 mg | 2006.31 mg | 0.14 mg | two very small pits |
| L' | 1984.98 mg | 1984.98 mg | 0 mg | no corrosion |

TABLE 4

| Test Solution | % Corrosion Inhibition Relative to "A'" | % Corrosion Inhibition Relative to "C'" |
|---|---|---|
| A' | — | — |
| B' | 74.4% | — |
| C' | −38.0% | — |
| D' | 35.6% | 53.3% |
| E' | 28.4% | 48.1% |
| F' | 57.2% | 69.0% |
| G' | 59.2% | 70.4% |
| H' | 69.2% | 77.7% |
| I' | 71.6% | 79.4% |
| J' | 80.0% | 85.5% |
| K' | 94.4% | 95.9% |
| L' | 100% | 100% |

TABLE 5

| Test Solution | % Corrosion Inhibition Compared To same solutions without Amine Oxide | Comparison Solution Code |
|---|---|---|
| B' | 74.4% | A' |
| D' | 53.3% | C' |
| F' | 40.2% | E' |
| H' | 24.5% | G' |
| J' | 29.6% | I' |

CONCLUSION

A solution of 0.02% sodium hypochlorite in water was very corrosive to the steel scalpel blades. The addition of the amine oxide to the hypochlorite reduced the corrosion. Buffering the sodium hypochlorite solutions to pH 7.5 with monopotassium phosphate increased the corrosion by 38%. The addition of the amine oxide reduced corrosion of the buffered hypochlorite by 53.3%. The addition of increasing amounts of dipotassium phosphate to the sodium hypochlorite solution, and buffering the solution to a pH of 7.5 with monopotassium phosphate, provided increasing corrosion inhibition. In each solution studied, greater corrosion inhibition was obtained when the amine oxide was included. Solution "L'" did not cause corrosion of the steel scalpel blades after a two hour exposure.

EXAMPLE III

Controlling corrosion of metals in NaOCl Solutions

PURPOSE

The purpose is to establish the minimum concentrations of phosphates needed to eliminate corrosion of surgical steel scalpel blades in a 0.02% sodium hypochlorite solution at pH 7.5.

MATERIALS

1. Sodium hypochlorite (from Purex Bleach)
2. Monopotassium phosphte ($KH_2PO_4$)
3. Dipotassium phosphate ($K_2HPO_4$)
4. Dimethyl lauryl amine oxide (30% active)
5. Disposable scalpel blades, #21 (Fisher Scientific Co. Cat. (#8-918-B)

TEST SOLUTIONS

R. 0.02% NaOCl, 0.025% $KH_2PO_4$, 0.35% amine oxide
S. 0.02% NaOCl, 1% $K_2HPO_4$, 0.167% $KH_2PO_4$, 0.35% amine oxide
T. 0.02% NaOCl, 1.2% $K_2HPO_4$, 0.233% $KH_2PO_4$, 0.35% amine oxide
U. 0.02% NaOCl, 1.4% $K_2HPO_4$, 0.267% $KH_2PO_4$, 0.35% amine oxide
V. 0.02% NaOCl, 1.6% $K_2HPO_4$, 0.33% $KH_2PO_4$, 0.35% amine oide
W. 0.02% NaOCl, 1.8% $K_2HPO_4$, 0.35% $KH_2PO_4$, 0.35% amine oxide
X. 0.02% NaOCl, 2.0% $K_2HPO_4$, 0.400% $KH_2PO_4$, 0.35% amine oxide
Z. 0.02% NaOCl, 2.2% $K_2HPO_4$, 0.433% $KH_2PO_4$, 0.35% amine oxide

PROCEDURE

Eight pairs of surgical disposable scalpel blades were accurately weighed on a Sartorius Microbalance. Each pair of blades was put into a separate test solution and the blades were allowed to soak for four hours. At the end of the soaking period, the blades were removed from the solutions and any corrosion products formed on the blades were washed off. The blades were then dried at room temperature for at least one hour and then reweighed. The weight loss for each pair of blades was computed.

RESULTS

TABLE 6

| TEST SOLUTION | INITIAL WEIGHT | FINAL WEIGHT | WEIGHT LOSS | VISIBLE OBSERVATIONS |
|---|---|---|---|---|
| R. | 2018.69 mg | 2016.20 mg | 2.49 mg | much corrosion |
| S | 2002.82 mg | 2002.65 mg | 0.17 mg | few pits |
| T. | 2009.89 mg | 2009.82 mg | 0.07 mg | two visible pits |
| U. | 1984.31 mg | 1984.29 mg | 0.02 mg | no visible corrosion |
| V. | 1974.62 mg | 1974.60 mg | 0.02 mg | no visible corrosion |
| W. | 1982.88 mg | 1982.87 mg | 0.01 mg | no visible corrosion |
| X. | 2013.87 mg | 2013.87 mg | 0 mg | no visible corrosion |
| Z. | 1967.18 mg | 1967.17 mg | 0.01 mg | no visible corrosion |

TABLE 7

| TEST SOLUTION | % INHIBITION OF CORROSION RELATIVE TO TEST SOLUTION "R" |
|---|---|
| S. | 93.2% |
| T. | 97.2% |
| U. | 99.2% |
| V. | 99.2% |
| W. | 99.6% |
| X. | 100% |
| Z. | 99.6% |

CONCLUSION

No detectable corrosion was found in Solutions "U" through "Y".

A 93 to 97% reduction in corrosion occurred in solutions "S" and "T".

EXAMPLE IV

Controlling Corrosion in NaOCl Solutions

PURPOSE

The purpose of this experiment is to establish the minimum concentration of phosphates needed to eliminate corrosion of surgical steel scalpel blades in a 0.5% sodium hypochlorite solution at pH 7.5.

MATERIALS
1. Sodium hypochlorite (from Purex Bleach)
2. Monopotassium phosphates (KH2PO4)
3. Dipotassium phosphate (K2HPO4)
4. Dimethyl lauryl amine oxide
5. Disposable scalpel blades, #21 (Fisher Scientific Co. Cat. #8-918-B)

TEST SOLUTIONS

M' 0.5% NaOCl, 0.35% amine oxide, 0.500% KH2PO4
N' 0.5% NaOCl, 0.35% amine oxide, 1% K2HPO4, 0.633% KH2PO4
O' 0.5% NaOCl, 0.35% amine oxide, 2% K2HPO4, 0.967% KH2PO4
P' 0.5% NaOCl, 0.35% amine oxide, 4% K2HPO4, 1.40% KH2PO4
R' 0.5% NaOCl, 0.35% amine oxide, 6% K2HPO4, 2.00% KH2PO4*
S' 0.5% NaOCl, 0.35% amine oxide, 8% K2HPO4, 2.53% KH2PO4**
T' 0.5% NaOCl, 0.35% amine oxide, 10% K2HPO4, 3.48% KH2PO4***
U' 0.5% NaOCl, 0.35% amine oxide, 12% K2HPO4, 3.77% KH2PO4****

*Solution R' turned cloudy after standing for 1¾ hours Solution S' turned cloudy after standing for ½ hour *Solution T' turned cloudy when titrating with KH2PO4 at pH 7.5 ****Solution U' turned cloudy when titrating with KH2PO4 at pH 7.5

V' 0.5% NaOCl, 0.35% amine oxide, 14% K2HPO4, 4.13% KH2PO4*****
W' 0.5% NaOCl, 0.35% amine oxide, 16% K2HPO4, 4.90% KH2PO4******

*****Solution V' turned cloudy when titrating with KH2PO4 at 7.8
******Solution W' turned cloudy when titrating with KH2PO4 at 8.0
NOTE: The cloudiness did not affect the effectiveness of the solutions.

PROCEDURE

Ten pairs of surgical disposable scalpel blades were accurately weighed on a Sartorius Microbalance. Each pair of blades were immersed in separate test solutions and allowed to soak for two hours. At the end of the soaking period, the blades were removed from the test solutions and any corrosion products were washed off. The blades were then room air dried for at least one hour and then reweighed. The weight loss for each pair of blades was computed.

RESULTS

TABLE 8

| TEST SOLU-TION | INITIAL WEIGHT | FINAL WEIGHT | WEIGHT LOSS | VISIBLE OBSER-VATIONS |
|---|---|---|---|---|
| M' | 2043.15 mg | 2033.52 mg | 9.63 mg | gross corrosion |
| N' | 2033.28 mg | 2022.29 mg | 10.99 mg | gross corrosion (worse than "M") |
| O' | 2024.60 mg | 2018.04 mg | 6.56 mg | many large pits |
| P' | 2016.91 mg | 2016.81 mg | 0.10 mg | few very small pits |
| R' | 2022.33 mg | 2022.25 mg | 0.08 mg | very few very small pits |
| S' | 2034.16 mg | 2034.10 mg | 0.06 mg | 3 or 4 tiny pits |
| T' | 2016.97 mg | 2016.97 mg | 0 mg | no visible corrosion |
| U' | 1993.69 mg | 1993.69 mg | 0 mg | no visible corrosion |
| V' | 1985.00 mg | 1985.00 mg | 0 mg | no visible corrosion |
| W' | 2000.89 mg | 2000.89 mg | 0 mg | no visible corrosion |

TABLE 9

| TEST SOLU-TION | TOTAL % PHOSPHATES AS $H_2PO_4$ AND $HPO_4$ | % CORROSION INHIBITION COMPARED TO TEST SOLUTION "M'" |
|---|---|---|
| M' | 0.390% | — |
| N' | 1.04% | −14.1% |
| O' | 1.86% | 31.9% |
| P' | 3.29% | 99.0% |
| R' | 4.86% | 99.2% |
| S' | 6.38% | 99.4% |
| T' | 8.22% | 100% |
| U' | 9.55% | 100% |
| V' | 10.93% | 100% |
| W' | 12.63% | 100 % |

CONCLUSION

Complete corrosion inhibition of surgical steel scalpel blades in 0.5% sodium hypochlorite was obtained by the addition of 6.38% (and greater) total phosphates as H2PO4 and HPO4.

EXAMPLE V

Sterilization Testing of Test Solution Q

PURPOSE

To demonstrate that a one day old test solution can sterilize one million spores of Bacillus subtilis var. globigii inoculated from a hard water suspension onto aluminum foil carriers.

MATERIALS
1. Test Solution Q—activated with hard water
   0.2% sodium hyphochlorite
   0.35% dimethyl lauryl amine oxide (30% active)
   9% dipotassium phosphate
   2% monopotassium phosphate
2. Bacillus subtilis var. globigii spores in ethanol
3. Aluminum foil strips
4. Culture broth—formula in grams per liter
   5 gm peptone
   3 gm beef extract
   3 gm yeast extract
   2 gm dextrose
   3 gm sodium sulfite
   3 gm ammonium sulfate
   10 ml Tween 80
   0.7 gm lecithin
5. Hard water—0.304 gm CaCl2+0.14 gm MgCl2 6 H20/Liter

METHOD

1. A quantity of spores in ethanol was centrifuged at 3000 rpm for 20 minutes and the ethanol was decanted. The spores were resuspended in sufficient sterile hard water so that the spore count was approximately 2,000,000 spores per 0.05 ml. of inoculum.

2. Each of 25 aluminum foil carriers was inoculated with 0.05 ml of the spore/hard water suspension. The inoculum was allowed to dry onto the carriers at room temperature for five days.

3. Twenty inoculated and dried carriers were immersed in a one day old Test Solution Q. The carriers were removed after 15 minutes of exposure and aseptically transferred to individual tubes of culture broth. All cultures were incubated for seven days at 37° C.

4. 0.2 ml of Test Solution Q was added to a tube of culture broth. One inoculated and dried carrier was added to the culture tube and incubated at 37° C. The purpose of this test was to determine if there was any growth inhibitory effect of the solution on the germinating spores.

5. One tube of culture broth was incubated with an inoculated carrier to serve as a positive control.

6. The number of viable spores on a carrier was determined by washing the spores off of the carrier with an ultrasonic cleaner into a 0.5% Tween 80 solution, and counting the spores in solution by the dilution/agar pour plate method.

RESULTS

Viable spore count—1,500,000 spores per carrier
Positive control—growth of *Bacillus globigii*
Inhibition control—growth of *Bacillus globigii*
Carriers exposed to Test Solution Q—no growth of *Bacillus globigii* in any of the 20 cultures.

CONCLUSION

No growth of Bacillus subtilis var. globigii occurred in any of the twenty tubes of culture broth incubated with aluminum foil carriers exposed to a one day old Test Solution Q for 15 minutes. The growth of Bacillus globigii which occurred in the culture tube inoculated with 0.2 ml of Test Solution Q and incubated with an inoculated carrier, demonstrated that all of the solution capable of exerting a growth inhibiting effect on the germinating spores had been effectively neutralized by the culture broth.

It is therefore concluded that all twenty aluminum foil carriers inoculated with a hard water suspension of Bacillus subtilis var. globigii were successfully sterilized by Test Solution Q using a 15 minute exposure time.

EXAMPLE VI

Disinfection of Salmonella with Test Solution Q

PURPOSE

To demonstrate that a two day old Test Solution Q can disinfect *Salmonella choleraesuis*, inoculated from a hard water suspension onto stainless steel penicylinders, using a one minute exposure time.

MATERIALS

1. Test Solution Q—activated using hard water
2. *Salmonella choleraesuis* A.T.C.C. #10708
3. Stainless steel penicylinders (Fisher Cat. #7-907-5)
4. 0.1% *Asparagine* (*Bacto*)
5. Nutrient broth—formula in grams per liter
10 gm peptic digest of animal tissue
5 gm beef extract
5 gm sodium chloride
6. Culture broth—formula in grams per liter
5 gm peptone
3 gm beef extract
3 gm yeast extract
2 gm dextrose
3 gm sodium sulfite
3 gm ammonium sulfate
10 ml Tween 80
0.7 gm Lecithin
7. Hard water—formula in grams per liter
0.304 gm Calcium chloride
0.139 gm Magnesium chloride hexahydrate

METHOD 1. 65 stainless steel penicylinders were washed in 1 M NaOH and rinsed thoroughly. The washed penicylinders were placed in a flask, covered with 0.1% Asparagine, and autoclaved for 15 minutes at 121 degrees C.

2. The contents of six tubes, each containing 10 ml of a 48 hour nutrient broth culture of *Salmonella choleraesuis*, were aseptically poured into sterile centrifuge tubes. The culture was centrifuged at 3000 rpm for 15 minutes and the supernatant liquid was decanted. The microorganisms were resuspended in 60 ml of sterile hard water.

3. The penicylinders were aseptically transferred to the hard water bacterial suspension and were allowed to soak in the suspension for 15 minutes. The penicylinders were then removed and placed vertically in a sterile petri dish matted with two sterile circles of filter paper. The inoculated penicylinder were dried in an incubator at 37 degrees C. for 25-35 minutes.

4. Sixty inoculated and dried penicylinders were soaked in a two day old Test Solution Q for 1 minute and transferred to individual tubes of culture broth. All cultures were incubated at 37 degrees C. for 3 days.

5. One penicylinder, unexposed to Test Solution Q, was placed in a culture broth tube and incubated to serve as a positive control.

6. 0.2 ml of Test Solution Q was added to a tube of culture broth. One penicylinder was then placed in the broth and incubated. This test served to detect unneutralized chlorine that might inhibit growth of microorganisms.

7. One inoculated and dried penicylinder was shaken in 9.0 ml of sterile saline for three minutes. The number of viable microorganisms in the resulting solution was determined by the dilution/agar pour plate method.

RESULTS

Viable microorganisms on a penicylinder=300,000
Positive control—positive growth of Salmonella
Inhibition control—positive growth of Salmonella
60 penicylinders exposed Test Solution Q for one minute—
No growth of Salmonella in 59 cultures
Growth of Salmonella occurred in 1 culture

CONCLUSION

Growth of *Salmonella choleraesuis* occurred in only one of the sixty tubes containing penicylinders exposed to Test Solution Q. No inhibition was noted due to unneutralized solution. It is therefore concluded that 59 of the 60 stainless steel penicylinders, inoculated with 300,000 organisms of *Salmonella choleraesuis* in a hard water suspension, were successfully sterilized by Test Solution Q using a one minute exposure.

EXAMPLE VII

Kelsey-Sykes "Clean" Disinfectant Test using Test Solution Q

MATERIALS

1. Test Solution Q
2. Test Organisms
   a. Staphylococcus aureus A.T.C.C. #6538
   b. Pseudomonas aeruginosa A.T.C.C. #15542
   c. Pseudomonas aeruginosa A.T.C.C. #27835
   d. Escheerichia coli A.T.C.C. #25922
   e. Salmonella choleraesuis A.T.C.C. #10708
   f. Klebsiella pneumoniae A.T.C.C. #13883
3. Medium for growth of test organisms—Bacto Synthetic Broth AOAC Code No. 0352 to which 0.1 ml of 10% dextrose has been added per 10 ml tube of broth.
4. Recovery Broth—Nutrient broth (BBL) containing 3% Tween 80 (10 ml per tube)
5. Standard Hard Water—0.304 gm CaCl2, 0.139 gm MgCl2 6H20/liter

METHOD

1. The Test Solution Q was diluted and activated by adding 3 parts of standard hard water to one part of Test Solution Q concentrate. The following test was performed using each of the microorganisms cited in "Materials", on a one day and a two day old Activated Test Solution Q.

2. Daily subcultures of each test organism were grown in 10 ml quantities of Synthetic broth. The subcultures were incubated for 24 hours at 37 degrees C. Daily subcultures were made for at least five days but less than fourteen days.

3. A 24 hour subculture of each test organism was centrifuged at 3,000 rpm for 15 minutes and the supernatant liquid was removed. Each test organism was resuspended in 10 ml of sterile standard hard water and shaken for one minute with a few glass beads. The 10 ml water/organism suspension of each test organism was used as the inoculum for the test.

4. The following procedure was used for each test organism.

5. Three ml of Activated Test Solution Q were pipetted into a 50 ml uncovered glass beaker. One ml of test inoculum was added to the Test Solution Q and the contents were mixed. Thirty seconds after the addition, 0.02 ml of the Test Solution Q/inoculum mixture was added to each of five recovery broths.

6. Ten minutes after the first addition, a second one ml inoculum was added to the Test Solution Q mixture and the contents were shaken. Thirty seconds after the second addition, 0.02 ml of the Test Solution Q mixture was added to each of five recovery broths.

7. Twenty minutes after the first addition, a third one ml inoculum was added to the Test Solution Q mixture and the contents were shaken. Thirty seconds after the third addition, 0.02 ml of the Test Solution Q mixture was added to each of five recovery broths.

8. All inoculated recovery broths were incubated at 37 degrees C. for 48 hours.

9. A microorganism count was performed on each test organism inoculum by dilution in sterile water and preparation of agar pour plates of each dilution. Colonies were counted after 2 days incubation at 37 degrees C.

10. All recovery broths showing no growth after 2 days of incubation were inoculated with a 1:1000 dilution of test organism culture and reincubated for an additional 1 day. This test served to show the presence of any inhibitory substance transferred to the recovery broth tubes. Positive growth indicates no inhibition.

Both a one day and a two day old Test Solution Q passed the Kelsey-Sykes Disinfectant test under "clean" conditions using a 30 second exposure time.

EXAMPLE VIII

The effect of the concentration of dimethyl lauryl amine oxide on silk suture loop sinking time

PURPOSE

To determine the optimal concentration of dimethyl lauryl amine oxide necessary to rapidly eliminate air bubbles from standard A.O.A.C. style silk suture loops and cause them to sink in an aqueous solution.

MATERIALS

1. Dimethyl lauryl amine oxide (30% active)
2. Tap water
3. Silk suture loops (prepared according to the A.O.A.C. specifications)
4. Stop watch
5. Beakers

PROCEDURE

1. Concentrations of 0.1, 0.15, 0.2, 0.25, 0.3, 0.35, 0.4 and 0.5% of amine oxide in tap water were prepared.

2. A suture loop sinking time test was performed on each solution. A stop watch was used to determine the interval between the time a suture loop was submerged in a test solution and the time at which the loop reached the bottom of the beaker.

3. At least four suture loops were tested in each solution. The average of all the test times for each solution was determined.

RESULTS

| (Average of 4 or more tests per solution) | |
|---|---|
| Concentration of Amine Oxide | Average Sinking Time (seconds) |
| 0.10% | 62 |
| 0.15 | 23 |
| 0.20 | 17 |
| 0.25 | 19 |
| 0.30 | 13 |
| 0.35 | 11 |
| 0.40 | 10 |
| 0.50 | 7 |

CONCLUSION

A rapid decrease in sinking time occurred when the concentration of amine oxide was increased from 0.1 to 0.2%. Above 0.3%, smaller additional decreases in sinking times were noted.

RESULTS:
Culture Codes: + = positive growth
0 = no growth

| Test solution Q | Test Organism | Count/ml | Recovery Broths (1) | (2) | (3) |
|---|---|---|---|---|---|
| 1 day | Staph | $5.6 \times 10^8$ | 00000 | 00000 | 00000 |
| | Pseudomonas 15542 | $3.5 \times 10^9$ | 00000 | 00000 | 00000 |
| | Pseudomonas 27835 | $9.8 \times 10^8$ | 00000 | 00000 | 00000 |
| | E. coli | $5.5 \times 10^8$ | 00000 | 00000 | 00000 |
| | Salmonella | $1.0 \times 10^9$ | 00000 | 00000 | 00000 |
| | Klebsiella | $3.0 \times 10^9$ | 00000 | 00000 | 00000 |
| Inhibitory Test - all recovery broth tubes positive | | | | | |
| 2 days | Staph | $3.5 \times 10^8$ | 00000 | 00000 | 00000 |
| | Pseudomonas 15542 | $5.6 \times 10^8$ | 00000 | 00000 | 00000 |
| | Pseudomonas 27835 | $8.7 \times 10^8$ | 00000 | 00000 | 00000 |
| | E. coli | $4.3 \times 10^8$ | 00000 | 00000 | 00000 |
| | Salmonella | $7.4 \times 10^8$ | 00000 | 00000 | 00000 |
| | Klebsiella | $1.2 \times 10^9$ | 00000 | 00000 | 00000 |
| Inhibitory Test - all recovery broth tubes positive | | | | | |

CONCLUSION

EXAMPLE IX

Eye Irritation Testing of Test Solution Q

PURPOSE:

The purpose of this test was to determine if Test Solution Q is irritating to the eye when tested on rabbits using the method described by Dr. J. H. Draize.

MATERIALS:
1. Three healthy New Zealand white rabbits
2. Test Solution Q

PROCEDURE:

1. One tenth milliliter of freshly mixed Test Solution Q was instilled in the conjunctival sac of one eye in each of the three rabbits, with the other eye of each rabbit serving as the control. The treated eyes were not washed. Ocular reactions read at 24 and 48 hours.

2. Six days after the first treatment, two separate hourly conjunctival instillations of one tenth milliliter of freshly mixed Test Solution Q were performed using the same test eyes as in the first treatment. Again, the treated eyes were not washed. Ocular reactions were read at 24 and 48 hours.

3. Two days after the second treatment, three separate hourly conjunctival instillations of one tenth milliliter of freshly mixed Test Solution Q were performed using the same test eyes as in the first treatment. Again, the treated eyes were not washed. Ocular reactions were read at 24 and 48 hours.

4. Reactions were scored using the method suggested by Dr. Draize.

CONCLUSION:

On the basis of the data presented herein, Test Solution Q is not an irritant to the rabbit eye when tested according to the method suggested by Dr. J. H. draize and described in "Appraisal of the safety of Chemicals in Food, Drugs and Cosmetics", published by the Association of Food and Drug Officials of the United States.

| Rabbits #1 and #3 First, Second and Third Treatment Results | Days After Instillation: | |
|---|---|---|
| | 1 | 2 |
| I. Cornea | | |
| A. Opacity-Degree of Density (area which is most dense is taken for reading) | | |
| Scattered or diffuse area-details of iris clearly visible (1) | 0 | 0 |
| B. Area of Cornea Involved | | |
| One quarter (or less) but not zero (1) | 0 | 0 |
| Score equals A × B × 5   Total maximum = 80 | 0 × 0 × 5 = 0 | |
| II. Iris | | |
| A. Values | | |
| Folds above normal, congestion, swelling, circumcorneal injection (any one or all of these or combination of any thereof), iris still reacting to light (sluggish reaction if positive) (1) | 0 | 0 |
| Score equals A × 5   Total possible maximum = 10 | 0 × 5 = 0 | |
| III. Conjunctivae | | |
| A. Redness (refers to palpebral conjunctivae only) | | |
| Vessels definitely injected above normal (1) | 0 | 0 |
| B. Chemosis | | |
| Any swelling above normal (includes nictitating membrane) (1) | 0 | 0 |
| C. Discharge | | |
| Any amount different from normal (does not include small amount observed in inner canthus of normal animals) (1) | 0 | 0 |
| Score (A + B + C) × 2   Total maximum +20 | (0 + 0 + 0) × 2 = 0 | |

| Rabbit #2 First and Second Treatment Results | Days After Instillation: | |
|---|---|---|
| | 1 | 2 |
| I. Cornea | | |
| A. Opacity-Degree of Density (area which is most dense is taken for reading) | | |
| Scattered or diffuse area-details of iris clearly visible (1) | 0 | 0 |
| B. Area of Cornea Involved | | |
| One quarter (or less) but not zero (1) | 0 | 0 |
| Score equals A × B × 5   Total maximum = 80 | 0 × 0 × 5 = 0 | |
| II. Iris | | |
| A. Values | | |
| Folds above normal, congestion, swelling circumcorneal injection (any one or all of these or combination of any thereof), iris still reacting to light (sluggish reaction if positive) (1) | 0 | 0 |
| Score equals A × 5   Total possible maximum = 10 | 0 × 5 = 0 | |
| III. Conjunctivae | | |
| A. Redness (refers to palpebral conjunctivae only) | | |
| Vessels definitely injected above normal (1) | 0 | 0 |
| B. Chemosis | | |
| Any swelling above normal (includes nictitating membrane) (1) | 0 | 0 |
| C. Discharge | | |
| Any amount different from normal (does not include small amount observed in inner canthus of normal animals) (1) | 0 | 0 |
| Score (A + B + C) × 2   Total maximum = 20 | (0 + 0 + 0) × 2 = 0 | |

-continued

Rabbit #2
Third Treatment Results

|  | Days After Instillation: | |
|---|---|---|
|  | 1 | 2 |
| I. Cornea | | |
|   A. Opacity-Degree of Density (area which is most dense is taken for reading) | | |
|     Scattered or diffuse are-details of iris clearly visible (1) | 0 | 0 |
|   B. Area of Cornea Involved | | |
|     One quarter (or less) but not zero (1) | 0 | 0 |
|   Score eequals A × B × 5  Total maximum = 80 | 0 × 0 × 5 = 0 | |
| II. Iris | | |
|   A. Values | | |
|     Folds above normal, congestion, swelling, circumcorneal injection (any one or all of these or combination of any thereof), iris still reacting to light (sluggish reaction if positive) (1) | 0 | 0 |
|   Score equals A × 5  Total possible maximum = 10 | 0 × 5 = 0 | |
| III. Conjunctivae | | |
|   A. Redness (refers to palpebral conjunctivae only) | | |
|     Vessels definitely injected above normal (1) | 0 | 0 |
|   B. Chemosis | | |
|     Any swelling above normal (includes nictitating membrane) (1) | 0 | 0 |
|   C. Discharge | | |
|     Any amount different from normal (does not include small amount observed in inner canthus of normal animals) (1) | 1 | 0 |
|   Score (A + B + C) × 2  Total maximum = 20 | (1 + 0 + 0) × 2 = 2 | |

The multi-compartment pouch of this invention can be used for purposes other than an instrument sterilizing solution. For example, it may be used in conjunction with an antimicrobial agent. Thus, it is effective for storing other germicidal solutions, such as disinfectants for bodily tissues, the ingredients of which must be kept separated until mixed for use. Further, it is to be understood that the location of the solutions in the compartments can be varied and be within the scope of this invention. For example, the phosphate solution could be put in the middle compartment with a color indicator which disappears when contact with the hypochlorite occurs. As desired, the coloring agents may be omitted or substituted by other agents which are non-reactive to the other ingredients, in as much as the coloring agent is merely a tell-tale device. Also, any number of plurality of compartments may be utilized.

It will be understood that utilizing the first bath with the conditioning agents is not always essential, because the second chlorine-based sterilizing liquid bath, used alone, can still perform its function with its effectiveness being a matter of degree depending on the condition of the items being sterilized and their need for pre-conditioning treatment.

Although dimethyl lauryl amine oxide has been indicated as 30% active because of its commercial availability, other concentrations may be utilized and the amounts proportioned accordingly.

It is to be understood that the multi-compartment pouch of this invention, prior to filling with liquid components and complete sealing, is in and of itself an article of commerce. Thus the multi-compartment pouch may be initially made with filling openings for each compartment and subsequently sealed after being filled with the desired contents. For example, three of the side seams may be initially sealed before filling, and the final and fourth side seams sealed after filling. Pouches with other than four side seams may also be used.

What is claimed is:

1. A system for sterilizing medical articles including metal articles comprising a multi-compartment package having a plurality of sealed compartments for separately storing the components of a sterilizing liquid which components comprise a hypochlorite, phosphates and a surfactant which is compatible with said chlorine and said phosphates, said separately stored components being maintained in an inactivated condition in their respective sealed compartment to prolong shelf-life until ready for use, means on said multi-compartment package for simultaneously releasing said components from said multi-compartment package, and a vessel for receiving said simultaneously released components and in which said components are mixed to thereby activate said sterilizing solution and provide in said vessel an activated sterilizing solution which is substantially non-irritating to tissue and which comprises 0.02 to 1% of said hypochlorite, 1.4 to 20% of said phosphates as di(alkali metal) phosphate and 0.08% to 21% as mono(alkali metal) phosphate, and 0.1 to 0.5% of said surfactant which is compatible with said chlorine and said phosphate, with the proviso that the lower limit of said di(alkali metal) phosphate is 4% when the amount of said hypochlorite is from 0.5 to 1%, said percentages being based on weight (in grams) per 100 ml. of solution, said articles to be sterilized being placed in said vessel to contact said sterilizing solution to thereby effect sterilization of said articles free of deleterious effects on said metal medical articles.

2. A system according to claim 1 wherein one of said sealed compartments of said multi-compartment package contains an aqueous solution of:
    0.1 to 0.5 grams dimethyl lauryl amine oxide (30% active) for every 100 ml. of sterilizing liquid in said vessel.

3. A system according to claim 1 wherein one of said sealed compartments of said multi-compartment package contains an aqueous solution of:
    0.02 to 1 grams of sodium hypochlorite for every 100 ml. of sterilizing liquid in said vessel.

4. A system according to claim 1 wherein one sealed compartment of said multi-compartment package has the following contents or multiples thereof:

314 ml. water
360 g. dipotassium phosphate
80 g. monopotassium phosphate
0.12 g. sodium chromate a second sealed compartment has the following contents or multiples thereof:

14.1 ml. dimethyl lauryl amine oxide (30% active)
5.2 ml. 0.04% chlorophenol red solution
80.7 ml. water a third sealed compartment has the following contents or multiples thereof:

136 ml. 6% sodium hypochlorite such that when the contents of said multi-compartment package are transferred to said vessel and mixed with 3.3 liters of water or multiples thereof, 4 liters or multiples thereof of sterilizing solution are obtained.

5. A system according to claim 1 wherein said multi-compartment package comprises a plurality of layers of superimposed plastic film heat sealed at their edge portion to define a plurality of compartments each sealed from one another.

6. A system according to claim 5 wherein said plastic film has heat sealed lower edge portions which converge toward one another to form a funnel-like lower end portion on said multi-compartment package such that cutting through said funnel-like lower end through all of said superimposed layers of plastic film simultaneously opens all of said compartments so that the components in each compartment simultaneously flow out of the package and mix with one another to thereby activate said mixture.

7. A system for sterilizing medical articles including metal medical articles comprising a first package containing a conditioning solution which comprises conditioning agents for cleaning said articles and diluting and neutralizing chemical contaminants on said articles and also wetting said articles, a first vessel for receiving said conditioning solution from said first package at the time sterilization is to be effected, a multicompartment package having a plurality of sealed compartments for separately storing the components of a sterilizing liquid which components comprise a hypochlorite, phosphates, and a surfactant which is compatible with said chlorine and said phosphates, said separately stored components being maintained in an inactivated condition in their respective sealed compartment to prolong shelf-life until ready for use, means on said multi-compartment package for simultaneously releasing said components from said multi-compartment package, and a second vessel for receiving said simultaneously released components and in which said components are mixed to thereby activate said sterilizing solution which is substantially non-irritating to tissue and which comprises 0.02 to 1% of said hypochlorite, 1.4 to 20% of said phosphates as di(alkali metal) phosphate and 0.08 to 21% as mono(alkali metal) phosphate, and 0.1 to 0.5% of said surfactant which is compatible with said chlorine and said phosphate, with the proviso that the lower limit of said di(alkali metal) phosphate is 4% when the amount of said hypochlorite is from 0.5 to 1%, said percentages being based on weight (in grams) per 100 ml. of solution, said articles to be sterilized being first placed in said first vessel to contact said conditioning solution and then being transferred to said second vessel to contact said sterilizing solution to thereby effect sterilization of said articles free of deleterious effects on said metal medical articles.

8. A system according to claim 7 wherein said first package has the following contents or multiples thereof:

7.5 g. potassium pyrophosphate
7.5 g. tripotassium phosphate
38 ml. dimethyl lauryl amine oxide (30% active)
60 ml. water.

9. A system according to claim 7 wherein said first package has the following contents or multiples thereof:

7.5 g. potassium pyrophosphate
7.5 g. tripotassium phosphate
38 ml. dimethyl lauryl amine oxide (30% active)
0.0128 g. Pylam turquoise blue
3360 ml. water.

* * * * *